United States Patent
Brown et al.

(10) Patent No.: US 7,223,787 B2
(45) Date of Patent: May 29, 2007

(54) PRENYLATION INHIBITORS REDUCE HOST CELL PERMISSIVENESS TO VIRAL REPLICATION

(75) Inventors: Michael S. Brown, Dallas, TX (US); Jin Ye, Dallas, TX (US); Chunfu Wang, Dallas, TX (US); Rhea Sumpter, Jr., Dallas, TX (US); Joseph L. Goldstein, Dallas, TX (US); Michael Gale, Jr., Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 756 days.

(21) Appl. No.: 10/690,891

(22) Filed: Oct. 21, 2003

(65) Prior Publication Data
US 2005/0085529 A1    Apr. 21, 2005

(51) Int. Cl.
*A61K 31/40* (2006.01)
(52) U.S. Cl. .................................. 514/423
(58) Field of Classification Search .......... None
See application file for complete search history.

(56) References Cited

OTHER PUBLICATIONS

Su, et al., Genomic analysis of the host response to hepatitis C virus infection. PNAS 2002; 99(24):15669-15674.*

* cited by examiner

*Primary Examiner*—Bruce R. Campell
*Assistant Examiner*—Stuart W. Snyder
(74) *Attorney, Agent, or Firm*—Richard Aron Osman

(57) ABSTRACT

Permissiveness of human cells to replication of susceptible pathogenic human viruses is reduced by treating the cells with a selective inhibitor of prenylation of a host cell protein. Target viruses, especially Flaviviridae, are predetermined to lack a CXXX box and prenylated viral protein, and to be replication-dependent on host protein prenylation. The general method comprises (a) contacting human cells subject to infection by the virus with an effective amount of a selective inhibitor of a prenylation enzyme of the cells; and (b) confirming a resultant reduction in permissiveness of the cells to replication of the virus. Targeted enzymes include prenyl biosynthetic enzyme like HMG CoA reductase farnesyl and/or geranylgeranyl transferase enzymes.

15 Claims, No Drawings

PRENYLATION INHIBITORS REDUCE HOST CELL PERMISSIVENESS TO VIRAL REPLICATION

This work was supported by National Institute of Health Grants HL-20948 and AI48235. The U.S. government may have rights in any patent issuing on this application.

FIELD OF THE INVENTION

The field of the invention is the use of prenylation inhibitors to reduce host cell permissiveness to replication of non-prenylated viruses.

BACKGROUND OF THE INVENTION

Approximately 170 million people worldwide are persistently infected with hepatitis C virus (HCV) and these individuals account for a majority of all cases of chronic liver disease (1). The public health impact of HCV is compounded by the overall low response rate to current interferon (IFN)-based therapies for treating HCV infection, underscoring the need for new therapeutic strategies to combat the HCV pandemic. HCV is a single-stranded positive sense RNA virus and member of the Flaviviridae (2). The 9.6-kilobase HCV genome encodes a single polyprotein that is post-translationally processed into at least 10 individual structural and nonstructural (NS) viral proteins, the latter of which are sufficient to support HCV RNA replication (3). Current studies support a model in which HCV infection results in assembly of the viral RNA and NS proteins into a replication complex that associates with the host cell endoplasmic reticulum (ER). Viral-directed processes convert the ER into a membranous web conducive to virus replication (4-6). The cellular co-factors and membrane constituents that contribute to assembly and maintenance of the HCV replication complex are not known.

West Nile (WN) virus is a member of the Flavivirus genus, which encompasses small spherical enveloped viruses harboring a single (+) RNA genome. Flavivirus genomic RNA is the only virus-specific mRNA in infected cells, encoding a single polyprotein, which is processed into structural and nonstructural viral proteins. Human infections with WN virus generally result in mild undifferentiated fever; however recent outbreaks of WN infection in North America, Europe and Israel have been characterized by relatively high rates of potentially fatal neurological disorders. See, Shi et al., 2002, J Virol 76, 5847-56; Yamshchikov et al., 2001, Virol 281, 294-304.

Cell membrane composition is subject to modification through the mevalonate pathway, which produces cholesterol and non-sterol isoprenoid products (7). Two of the mevalonate-derived isoprenoids, farnesyl (15 carbons) and geranylgeranyl (20 carbons), are attached to membrane proteins via formation of a cysteine thioether (7, 8). This process, called protein prenylation, targets certain proteins to cell membranes where they regulate many cellular functions, ranging from vesicle budding and fusion to growth regulation. Therapeutic control of the mevalonate pathway has proven effective for the clinical treatment of hypercholesterolemia and is achieved in part through the use of statin compounds (7, 9). Statins block mevalonate production by inhibiting 3-hydroxy-3-methylglutaryl coenzyme A reductase (HMG CoA reductase), resulting in a block in the subsequent steps of cholesterol synthesis (7, 9). At the high concentrations that are attainable in tissue culture cells, statins deplete mevalonate sufficiently to lower the cellular pools of farnesyl and geranylgeranyl pyrophosphates, which are the donors in the protein prenylation reactions (7, 10).

Here we disclose that HCV replication requires host protein prenylation. We further disclose that WN virus replication also requires host protein prenylation. We further disclose that prenylation inhibitors can be used to reduce host cell permissiveness to these and other viruses, particularly Flaviviridae, that do not have any prenylated viral proteins. The strict dependence of viral replication upon host protein prenylation provides a therapeutic approach for treating infection by these viruses.

Relevant Literature

Bordier et al. (2003, J. Clin. Invest. 112:407-414, 2003) report in vivo antiviral efficacy of prenylation inhibitors against hepatitis delta virus (HDV), building on prior work suggesting that HDV encodes farnesylated viral proteins, and that replication of this virus may be inhibited by an HMG CoA reductase inhibitor and a farnesyl transferase inhibitor. Bordier et al. suggests that targeting viral prenylation may provide a strategy for other medically important viruses, citing Glenn, J. S. (1995, Prenylation and virion morphogenesis. In The unique hepatitis delta virus. G. Dinter-Gottlieb, editor. R.C. Landes Publishing Co. Austin, Tex., USA. 83-93). This chapter suggests that CXXX prenylation boxes are found in hepatitis A virus, foot and mouth disease virus, and the white clover mosaic virus.

Glenn has issued several U.S. Patents describing HDV inhibition and further suggesting extrapolating their HDV treatment to other viruses that have prenylated proteins. For example, U.S. Pat. No. 6,159,939 suggests screening sequence banks for viral proteins containing a C-terminal CXXX box, and suggests inhibiting the prenylation of prenylated viral proteins of such viruses (col.7, lines 23-26). However, screening the recited viruses for CXXX boxes reveals that none of them contains a C-terminal CXXX box, nor do any of them encode a prenylated viral protein: reports of prenylated viral protein are limited to HDV and ECV (below).

Thome et al. (2001, JCB 152, 1115-22) report that equine herpes virus (ECV) encodes a protein (v-E10) that contains a C-terminal geranylgeranyltransferase II consensus site and that lovastatin can reduce membrane localization of v-E10. ECV is a DNA virus with distinct structure and replication mechanisms from RNA viruses such as Flaviviridae.

Gower and Graham (2001, Antimicrobial Agents and Chemotherapy 45, 1231-37) report antiviral activity of lovastatin against respiratory syncytial virus (RSV), and suggest that RSV replication is dependent on RhoA geranylgeranylation. RhoA geranylgeranylation is mediated by GGTase II, and RSV structure and replication are distinct from Flaviviridae and Picornaviridae.

SUMMARY OF THE INVENTION

The invention provides methods and compositions for reducing permissiveness of human cells to replication of certain pathogenic human viruses by treating the cells with a selective inhibitor of prenylation of a host cell protein. Target viruses are predetermined (I) to lack prenylated viral protein, and (ii) to be replication-dependent on host protein prenylation. The general method comprises reducing permissiveness of human cells to replication of a pathogenic human virus predetermined to lack prenylated viral protein, and to be replication-dependent on host protein prenylation by (a) contacting human cells subject to infection by the virus with an effective amount of a selective inhibitor of a prenylation enzyme of the cells; and (b) confirming a resultant reduction in permissiveness of the cells to replication of the virus.

In one embodiment, the invention provides a method for reducing permissiveness of human cells to replication of a pathogenic human virus predetermined to lack prenylated viral protein, and to be replication-dependent on host protein geranylgeranylation by (a) contacting human cells subject to infection by the virus with an effective amount of a selective inhibitor of a geranylgeranyl transferase I (GGTase I) of the cells; and (b) confirming a resultant reduction in permissiveness of the cells to replication of the virus.

Any method-compatible GGTase I-selective inhibitor (e.g. GGTI-286) may be used; and the method is applicable to a wide variety of viruses predetermined to lack prenylated viral protein and to be dependent on host protein geranylgeranylation, including hepatitis C virus (HCV).

In another embodiment, the invention provides a method for reducing permissiveness of human cells to replication of a pathogenic human Flaviviridae (and also Picornaviridae) virus predetermined to lack prenylated viral protein, and to be replication-dependent on host protein prenylation by (a) contacting human cells subject to infection by the virus with an effective amount of a selective inhibitor of a prenylation enzyme of the cells; and (b) confirming a resultant reduction in permissiveness of the cells to replication of the virus.

Any method-compatible prenylation inhibitor may be used, particularly selective inhibitors of a rate-limiting prenyl biosynthetic enzyme like HMG CoA reductase (e.g. lovastatin) and selective inhibitors of farnesyl and/or geranylgeranyl transferase enzymes. The method is applicable to a wide variety of Flaviviridae viruses predetermined to lack prenylated viral protein and to be dependent on host protein prenylation, including West Nile (WN) virus, and HCV.

The invention also provides disclosed method-corresponding compositions, kits, instructions and business methods for reducing permissiveness of human cells to replication of certain pathogenic human viruses. Particular kits comprise a disclosed inhibitor pharmaceutical composition packaged with instructions reciting a subject method.

DETAILED DESCRIPTION OF PARTICULAR EMBODIMENTS OF THE INVENTION

In one aspect, the invention discloses that selective and specific inhibitors of prenyl biosynthetic or prenyltransferase enzymes can reduce host cell permissiveness to certain susceptible viruses predetermined to lack any prenylated viral protein. This is the first report that prenylation inhibitors, such as HMG CoA reductase inhibitors or GGTase I inhibitors, can inhibit Flaviviridae-type viral replication. Hence, candidate target viruses are pathogenic (i.e. disease-associated), preferably human pathogenic, Flaviviridae (and some Picornaviridae) viruses that replicate in the host cytoplasm, require a prenylated host protein for cytoplasmic membrane anchoring, and are predetermined to lack any prenylated viral protein. Preferred targets do not comprise, or are predetermined not to comprise by sequence analysis any even putative C-terminal CXXX boxes. Preferred target Flaviviridae are hepaciviruses such as HCV, GB virus A, GB virus B and GB virus C; flaviviruses such as yellow fever virus, West Nile virus, and Dengue fever virus; and pestiviruses, such as bovine diarrhea virus and classical swine fever virus. Picornaviridae targets include poliovirus and foot and mouth disease virus.

In another aspect, the invention discloses that replication of certain susceptible viruses is dependent on host protein geranylgeranylation (GGTase I activity), and that selective inhibitors of GGTase I can reduce host cell permissiveness to these viruses. This is the first report that GGTase I inhibitors can inhibit viral replication. Hence, candidate target viruses of this aspect of the invention further encompass RNA viruses that have similar host prenylation-dependent cytoplasmic-membrane associated replication but disparate genome and/or virion structure. Preferred additional target viruses are disease-associated, positive-sense viruses, preferably encoding a single mRNA, particularly Flaviviridae and Picornaviridae. Particular additional targets are pathogenic paramyxoviruses, such as RSV, parainfluenza virus, New Castle disease virus, Measles virus and mumps virus; Caliciviruses, such as hepatitis E virus and Norwalk virus; Togaviruses, such as Sindbis virus and Rubella virus; Rhabdoviruses, such as Vesicular stomatitis virus and rabies virus; Bunyaviruses, such as Hantaan virus, La Crosse virus and Rift valley fever virus; Coronaviruses, such as the SARS virus and human corona virus; Arenaviruses, such as lymphocytic choriomeningitis virus; filoviruses, such as Ebola virus and Marburg virus; etc.

A wide variety of method-compatible prenyl biosynthetic enzyme inhibitors are well-known in the art, and any method-compatible selective inhibitors of the targeted enzyme may be used, such as inhibitors targeting biosynthetic enzymes of the mevalonate pathway, or the biosynthetic pathway from mevalonate to prenyl lipids farnesyl and geranylgeranyl, particularly rate-limiting enzymes, particularly wherein the enzyme is HMG CoA reductase or geranylgeranyl transferase I (GGTase I). Preferred are HMG CoA reductase inhibitors, particularly the statin drugs such as atorvastatin (Lipitor), pravastatin (Pravachol), lovastatin (Mevacor), simvastatin (Zocor), fluvastatin (Lescol) and rosuvastatin calcium (Crestor). In addition, a variety of prenyltransferase inhibitors are well-known in the art, including farnesyl transferase inhibitors such as R115777 (Zarnestra), L-744,832, A-176120, BZA-5B, FTI-277 and RPR130401 (for reviews, see Ayral-Kaloustian et al., Curr Med Chem. 2002 May 1;9(10):1003-32; Gibbs et al., 1997, Annu Rev Pharmacol Toxicol 37, 143-66); geranylgeranyl transferase inhibitors, particularly GGTase I inhibitors including GGTI-286, GGTI-298, Massadine (Nishimura et al., Org Lett. 2003 Jun. 26;5,2255-7), and Candida albicans GGTase I inhibitors, e.g. Murthi, et al. (Bioorg Med Chem Lett. 2003 Jun. 2;13:1935-7); Sunami et al. (Bioorg Med Chem Lett. 2002 Feb. 25;12:629-32); and GGTase II inhibitors such as NE10790.

The recited inhibitor functionally and selectively inhibits the catalytic activity of the target enzyme, which inhibition may be competitive, or non-competitive, covalent or non-covalent. However, selective inhibitors of the target enzymes do not encompass compounds like 25-hydroxycholesterol that may indirectly affect these enzymes through changes in enzyme availability (e.g. transcription, translation, etc.), rather than activity per se. Preferred inhibitors are relatively selective for the target enzyme, showing at least a 50%, preferably at least a 2-, 3- or 5-fold preference for the target enzyme; hence, preferred geranylgeranyl transferase inhibitors preferentially inhibit geranylgeranyl transferases over farnesyl transferases; preferred GGTase I-selective inhibitors preferentially inhibit GGTase I over Rab GGTase (GGTase II). More preferred inhibitors are specific to the targeted enzyme, presenting at least a 10-fold, preferably at least a 20-, 50-, 100-, or 1000-fold preference for the target enzyme. Preferred inhibitors provide target affinity or IC(50) of at least 1 mM, preferably at least 100 uM, 10 uM or 1 uM. Suitability of particular candidate target viruses and inhibitors is readily confirmed empirically using cell-based or in vivo virus replication assays, as described herein or in references cited herein, or otherwise known in the art.

The methods involve reducing permissiveness of cells to replication of a target pathogenic RNA virus predetermined to lack prenylated viral protein, and to be replication-dependent on host protein prenylation by the general method of: (a) contacting cells subject to infection by the target virus with an effective amount of a selective inhibitor of a prenylation enzyme of the cells; and (b) confirming a resultant reduction in permissiveness of the cells to replication of the virus. In preferred embodiments, the cells are human cells in situ, and the contacting step is effected by delivering to the human host a pharmaceutical composition comprising the inhibitor. The resultant reduction in host cell permissiveness to viral replication may be confirmed in any convenient manner, including directly, e.g. using biopsied cells, or indirectly or inferentially, e.g. by detecting a reduction in host viremia, a reduction in viral-associated pathology, etc.

The inhibitors are typically administered in the form of a pharmaceutical composition comprising at least one inhibitor, or prodrug inhibitor, and a carrier, vehicle or excipient suitable for use in pharmaceutical compositions. Without being limited thereto, such materials include diluents, binders and adhesives, lubricants, plasticizers, disintegrants, colorants, bulking substances, flavorings, sweeteners and miscellaneous materials such as buffers and adsorbents. Such carriers are well known in the pharmaceutical art as are procedures for preparing pharmaceutical compositions.

Depending on the intended route of delivery, the compositions may be administered in one or more dosage form(s) including, without limitation, liquid, solution, suspension, emulsion, tablet, multi-layer tablet, bi-layer tablet, capsule, gelatin capsule, caplet, lozenge, chewable lozenge, bead, powder, granules, dispersible granules, cachets, douche, suppository, cream, topical, inhalant, aerosol inhalant, patch, particle inhalant, implant, depot implant, ingestible, injectable, or infusion. The dosage forms may include a variety of other ingredients, including binders, solvents, bulking agents, plasticizers etc.

A wide variety of orally administerable compositions may be used. In a particular embodiment, the oral compositions are provided in solid discrete, self-contained dosage units, such as tablets, caplets, lozenges, capsules, gums, etc., which may comprise or be filled with liquid or solid dosage of the inhibitor. Orally administerable compositions can take the form of bulk liquid solutions or suspensions, or bulk powders, but are more commonly presented in unit dosage forms to facilitate accurate dosing.

The term "unit dosage forms" refers to physically discrete units suitable as unitary dosages for human subjects and other mammals, each unit containing a predetermined quantity of active material calculated to produce the desired therapeutic or prophylactic effect, in association with a suitable pharmaceutical excipient. Typical unit dosage forms include prefilled, premeasured ampules or syringes of the liquid compositions or pills, tablets, capsules or the like in the case of solid compositions. In such compositions, the inhibitor is usually a minor component (from about 0.1 to about 50% by weight or preferably from about 1 to about 40% by weight) with the remainder being various vehicles or carriers and processing aids helpful for forming the desired dosing form.

The compounds of this invention can be administered as the sole active agent or they can be administered in combination with other agents, including other target enzyme inhibitors. The administrable compositions disclosed herein are merely representative. Other materials as well as processing techniques and the like are set forth in Part 8 of Remington's Pharmaceutical Sciences, 17th edition, 1985, Mack Publishing Company, Easton, Pa., which is incorporated herein by reference.

The dosage forms of the present invention involve the administration of an active therapeutic substance or multiple active therapeutic substances in a single dose during a 24 hour period of time or multiple doses during a 24 hour period of time. The doses may be uneven in that each dose is different from at least one other dose. A wide variety of dosages may be used, depending on the application and empirical determination; typical dosages range from 10 ug to 1 g, preferably at least 100 ug, more preferably at least 1 mg, more preferably at least 10 mg, most preferably at least 100 mg.

The subject compositions may be administered to effect various forms of release, which include, without limitation, immediate release, extended release, controlled release, timed release, sustained release, delayed release, long acting, pulsatile delivery, etc., using well known procedures and techniques available to the ordinary skilled artisan. A description of representative sustained release materials can be found in the incorporated materials in Remington's Pharmaceutical Sciences.

The subject compositions may be formulated for administration by any route, including without limitation, oral, buccal, sublingual, rectal, parenteral, topical, inhalational, including itnranasal, injectable, including subcutaneous, intravenous, intramuscular, etc., topical, including transdermal, etc. The subject compositions are administered in a pharmaceutically (including therapeutically, prophylactically and diagnostically) effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

For the prevention and/or treatment of long-term conditions, such as chronic or latent infections, the regimen for treatment may stretch over many months or years so oral dosing is preferred for patient convenience and tolerance. When used to prevent infection or spread, the inhibitor may be administered to a patient at risk of infection or spread, typically on the advice and under the supervision of a physician.

EXAMPLES

Example I

Disruption of Hepatitis C Virus RNA Replication Through Inhibition of Host Protein Prenylation Here we report that HCV RNA replication and assembly of the viral replication complex require host protein prenylation. HCV RNA replication in human liver cells is disrupted by treatment with the HMG CoA reductase inhibitors, such as lovastatin or an inhibitor of protein geranylgeranyl transferase I, which induces the dissolution of the HCV replication complex. Viral replication is not affected by treatment of cells with an inhibitor of farnesyl transferase. When added to lovastatin-treated cells, geranylgeraniol, but not farnesol, restores replication complex assembly and viral replication.

The potential of statins to alter the sterol and protein composition of cellular membranes provides a unique tool to assess the role of these constituents in supporting HCV RNA replication. Since native HCV cannot be efficiently propagated in cultured cells (2), genome-length and subgenomic HCV RNA replicons have been developed to facilitate the study of viral replication. These HCV RNA replicon systems encompass either the entire HCV genome or only the NS3-5B protein coding region within a neomycin-selectable, bi-cistronic RNA. When introduced into human hepatoma (Huh7) cells, the HCV replicon RNA replicates autonomously on ER membranes, thereby approximating an HCV infection (3).

In the current study, we used Huh7 cell lines that harbor genome-length replicons (Huh7-C5B3 cells) or subgenomic replicons (Huh7-K2040 and Huh7-HP cells) (11-12) to examine the influence of lovastatin, the first clinically approved statin inhibitor of HMG CoA reductase, on HCV RNA replication. Huh7-HP cells are less sensitive to IFN than Huh7-K2040 cells (14), owing to adaptive mutations in the HCV genome that enhance RNA replication in tissue culture.

Lovastatin Reduces HCV RNA Levels. In the absence of lovastatin HCV RNA replication was robust and viral RNA and protein levels increased concomitantly with the culture density of Huh7-K2040 cells. Lovastatin treatment of Huh7-K2040 cell cultures reduced RNA levels more than 70% after a 24-hour treatment and more than 95% after 72 hours. The lovastatin-induced decline in HCV RNA abundance was first apparent between 12- and 24-hour post-treatment (14). The drop in viral RNA abundance was accompanied by a reduction in viral protein levels over a 72-hour culture period. A similar reduction in viral RNA was observed in lovastatin-treated Huh7-C5B3 and Huh7-HP cells (14). Lovastatin treatment also reduced the levels of viral proteins within Huh7-C5B3 and Huh7-HP cells. Thus, lovastatin suppressed HCV RNA and protein abundance irrespective of viral genome variation and potential phenotypic differences among cell lines.

Lovastatin slows the proliferation of some malignant cell types by indirectly suppressing DNA synthesis (15), which may negatively affect HCV RNA replication (16). We therefore examined the influence of lovastatin upon the synthesis of DNA, mRNA, and protein in Huh7-K2040 cells. Treatment of Huh7-K2040 cultures with lovastatin for 24 hours reduced HCV RNA levels to ~25% of untreated control cells, but did not significantly affect cellular DNA or mRNA synthesis. The incubation of parallel cultures with the DNA polymerase inhibitors aphidicolin or hydroxyurea blocked DNA synthesis, but did not affect viral RNA or cellular mRNA levels during a 24-hour culture period. Each compound moderately suppressed the global rate of cellular protein synthesis. At the concentrations used, lovastatin had no significant effects upon cell viability when cultures were treated over 7 days (14). Our results demonstrate an antiviral action of lovastatin that is not attributable to global effects upon cellular DNA, mRNA or protein synthesis. Rather, the data indicate that HCV RNA replication requires one or more products derived from mevalonate, the product of the HMG CoA reductase reaction (7).

Rescue by Mevalonate and Geranylgeraniol. To define the mevalonate-derived products required for HCV RNA replication, Huh7-K2040 cells were cultured with or without lovastatin in the absence or presence of various metabolites whose synthesis requires HMG CoA reductase. During a 24-hour culture period lovastatin treatment reduced HCV RNA levels to 10-20% of untreated control cultures, and this was unaffected when the culture medium was supplemented with exogenous cholesterol in the form of low density lipoprotein (LDL). On the other hand, mevalonate produced a dose-dependent rescue of HCV RNA levels, and the effect was enhanced by the presence of exogenous LDL. Mevalonate serves as precursor to cholesterol and isoprenoid biosynthesis (7). When cholesterol is not available, most mevalonate is directed into cholesterol. When LDL is available, the cholesterol demand is satisfied and more of the mevalonate is directed to non-sterol isoprenoids (17).

The results with LDL indicate that lovastatin treatment depletes the cells of one or more non-sterol end products of mevalonate metabolism that are required to support HCV RNA replication. To identify this end-product, we supplemented the lovastatin-treated cultures of Huh7-K2040 cells with the mevalonate-derived isoprenoids, geranylgeraniol or farnesol. In parallel control experiments we supplemented the cultures with oleate, a long-chain fatty acid that is not derived from mevalonate. Exogenous geranylgeraniol, but neither farnesol nor oleate, mediated a dose-dependent rescue of HCV RNA levels from the suppressive actions of lovastatin.

To demonstrate that lovastatin depletes cells of geranylgeranylated proteins, we subjected the proteins of Huh7-K2040 cells to SDS-PAGE and blotted with an antibody against Rap1a, a small GTP-binding protein that is known to be geranylgeranylated (8). Lovastatin caused the appearance of a slow-migrating form of Rap I a, which represents the unprenylated protein (21). Addition of geranylgeraniol, but not farnesol, eliminated the upper band, indicating restoration of geranylgeranylation. Our data showed that lovastatin reduced HCV RNA at the same concentrations in which it prevented geranylgeranylation of Rap 1a. Considered together, these results indicate that one or more geranylgeranylated proteins is required for HCV RNA replication and that lovastatin blocks HCV replication by depleting endogenous geranylgeranyl pyrophosphate, thereby preventing geranylgeranylation of the critical protein(s). Although Rap1a was used as an indicator of protein geranylgeranylation in this study, there is no evidence that it is the protein required for HCV RNA replication.

HCV Replication Complex Requires Protein Geranylgeranylation. Among other functions, geranylgeranylated proteins mediate the interaction of membranes with cytoskeletal proteins (8). Such interactions are likely to be required for the formation of the ER-associated HCV replication complex, which contains the viral RNA as well as the nonstructural viral proteins (1, 2). Using immunocytochemical techniques, we showed that HCV nonstructural proteins (NS3-NS5B) co-localize with viral RNA and appear in a punctate staining pattern associated with ER membranes. To test whether lovastatin affects the replication complex, we stained cells with an antibody to NS5A and an FITC-labeled second antibody. In the absence of lovastatin treatment, much of the NS5A was localized in a punctate pattern consistent with the ER localization of the HCV replication complex. After treatment with lovastatin for 48 hours, the punctate NS5A staining pattern largely disappeared, and the protein was diffuse throughout the cytoplasm. Incubation of the cells with geranylgeraniol, but not farnesol, prevented the loss of the punctate distribution. These data indicate that one or more geranylgeranylated proteins is required for the maintenance of the HCV replication complex.

A large class of geranylgeranylated proteins is synthesized by protein geranylgeranyl transferase 1 (GGTase I), which recognizes carboxyl terminal Cys-A-A-X sequences (CAAX boxes), where A is an aliphatic amino acid and X is typically leucine (8). The enzyme is closely related to protein farnesyl transferase, which recognizes CAAX boxes terminating in serine or methionine and transfers farnesyl instead of geranylgeranyl to the cysteine of the CAAX box (8). A second class of GGTases called Rab GGTase (or GGTase II) attaches geranylgeranyl only to Rab proteins, which lack CAAX boxes but contain COOH-terminal CXC or XXCC sequences (8). To determine whether GGTase I is required for HCV RNA replication, we treated Huh7-K2040 cells with increasing concentrations of two inhibitors based on CAAX boxes: the GGTase I inhibitor GGTI-286 (19) or the farnesyl transferase inhibitor FPTI-III (20).

Treatment with GGTI-286 resulted in a dose-dependent decrease in the level of HCV RNA. In contrast, FPTI-III had no effect on viral RNA levels. To confirm the specificity of GGTI-286 and FPTI-III action, we evaluated the effect of each compound on the prenylation of wild-type H-Ras, which is normally farnesylated, and a mutant H-Ras(S189L) in which the carboxyl-terminal amino acid has been changed to leucine, making it a substrate for GGTase 1 (21). Both Ras proteins showed an upper and lower band in the absence of inhibitors, indicating that prenylation was not complete, perhaps owing to overexpression. FPTI-III at 10 μM eliminated the lower band in the H-Ras blots, but had only a partial effect on the prenylation of H-Ras(S189L), consistent with preferential specificity for farnesyl transferase. GGTI-286 at 10 μM showed no such specificity, inhibiting farnesylation of H-Ras as well as geranylgeranylation of H-Ras (S189L). Furthermore, FPTI-III did not inhibit prenylation of the endogenous geranylgeranylated protein, Rap1a, even at doses up to 30 μM, whereas GGTI-286 showed clear-cut inhibitory effects of Rap1a at 10 μM. Inasmuch as FTP-III eliminated farnesylation, but failed to inhibit HCV RNA replication, we conclude that farnesylation is not required for this process. Thus, the inhibitory activity of GGTI-286 on HCV RNA replication must be due to its action against GGTase I, and not farnesyl transferase. Consistent with this conclusion, GGTI-286, but not FPTI-III, produced a redistribution of the HCV NS5A protein that was similar to that observed in lovastatin-treated cells, namely, a change from a punctate pattern to a diffuse pattern. Taken together, these results demonstrate a specific dependence upon protein geranylgeranylation for the localization and assembly of the HCV RNA replication complex.

We are unaware of previous data suggesting that inhibitors of GGTase I block virus replication. On the other hand, inhibitors of farnesyl transferase block the replication of hepatitis delta virus, which encodes a protein that terminates in a farnesyl-type CAAX box (22). However, the HCV genome does not encode any CAAX-terminating proteins, indicating that lovastatin and GGTI-286 inhibit HCV RNA replication by blocking the geranylgeranylation of a cellular protein rather than a viral protein. Recent studies of HCV showed that treatment with 25-hydroxycholesterol reduce the level of HCV replicon RNA within hepatoma cells, but the mechanism of this effect is unknown (23).

Both lovastatin and GGTI-286 acutely and markedly suppress HCV RNA levels, an effect that has not been observed heretofore with other drug treatments. The three HCV replicon-containing cell lines that we examined all contained genotype 1 HCV RNA, which is associated with the most severe clinical disease and has the poorest response rate to IFN-based therapy (25, 26). HCV replicates as populations of genetically distinct variants or quasispecies that are continuously generated, presumably owing to lack of proofreading by the viral NS5B RNA-dependent RNA polymerase (2, 27). Because viral genetic complexity provides a pool from which therapy-resistant variants can emerge (28, 29), the quasispecies nature of HCV has proved troublesome for contemporary antiviral therapeutic strategies and is certain to limit the benefits of future therapies that are directed against virus-specific targets (30). On the other hand, therapeutic approaches that target host-specific proteins required for HCV RNA replication, such as geranylgeranylated proteins, are much less likely to be affected by viral genetic variation.

In animal models, administration of statins in high doses inhibits the geranylgeranylation of Rap1a in tissues such as bone (31). In patients, however, in order for statins to inhibit HCV RNA replication, the drugs may have to be delivered to the liver in concentrations higher than those typically obtained at current therapeutic doses, and this may cause toxicity. Treatment with selective protein GGTase I inhibitors provides a preferred avenue of antiviral therapy that avoids such toxicity.

Example II

Disruption of West Nile Virus RNA Replication Through Inhibition of Host Protein Prenylation Here we report that WN virus replication and assembly of the viral replication complex require host protein prenylation. WN virus replication in several mammalian cell types, and in a mouse model is disrupted by treatment with the HMG CoA reductase inhibitors, such as lovastatin, as well as inhibitors of host protein prenylation. We adapted the protocols for the current study from Beasley et al., 2002, Virol 296, 17-23; and Shi et al., 2002, J Virol 76, 5847-56.

Cells and virus. Vero (ATCC CCL-81) cells are grown in minimal essential medium (MEM) supplemented with 10% fetal bovine serum (FBS). BHK-21/WI2 (BHK-21) and *Aedes albopictus* C6/36 (C6/36) (ATCC CRL-1660) cells are grown in Dulbecco's modification of MEM with 10% FBS and 0.1 mM nonessential amino acids. Antibiotics are added to all media at 10 U/ml of penicillin and 10 μg/ml of streptomycin. Cells are maintained in 5% $CO_2$ at 37° C. (Vero and BHK-21) or 28° C. (C6/36). West Nile viruses are obtained from the World Arbovirus Reference Collection and stocks are grown and plaque titrated in Vero cells. Prenylation inhibitors examined over a series of 10-fold dilutions. HMG CoA reductase inhibitors: atorvastatin (Lipitor), pravastatin (Pravachol), lovastatin (Mevacor), simvastatin (Zocor), and fluvastatin (Lescol) are obtained from the respective commercial vendors; farnesyl- and geranylgeranyltransferase inhibitors are provided as described herein.

IFA. Indirect immunofluorescence assays (IFA) are used to detect viral protein expression in WNV RNA-transfected BHK-21 cells. After electroporation, approximately $10^5$ transfected cells are spotted onto 10-mm glass coverslips. Cells on coverslips are analyzed by IFA at various times posttransfection for viral protein synthesis. Cells are fixed in 3.7% paraformaldehyde with PBS, pH 7.5, at room temperature for 30 min followed by incubation in −20° C. methanol for 30 min. The fixed cells are washed with PBS, incubated at room temperature for 45 min in WNV immune mouse ascites fluid (1:100 dilution; ATCC, Manassas, Va.), and further reacted with goat anti-mouse immunoglobulin G conjugated with fluorescein isothiocyanate at room temperature for 30 min (1:100 dilution) (KPL, Gaithersburg, Md.). The coverslips are washed with PBS, mounted to a slide using fluorescent mounting medium (KPL), and observed under a fluorescence microscope equipped with a video documentation system (Zeiss, Thornwood, N.Y.).

Specific infectivity assay. Approximately 10 µg of RNA is electroporated to $10^7$ BHK-21 cells, as described above. Both transfected and untransfected BHK-21 cells are adjusted to a concentration of $6\times10^5$ cells per ml. A series of 1:10 dilutions are made by mixing 0.5 ml of transfected cells with 4.5 ml of untransfected cells. One milliliter of cells ($6\times10^5$ cells total) for each dilution is seeded per individual well of six-well plates. Triplicate wells are seeded for each cell dilution. The cells are allowed to attach to the plates for 4 to 5 h under 5% $CO_2$ at 37° C. before the first layer of agar is added, as described previously (Reisen, et al. 1993. J. Med. Entomol. 30:151-160). After incubation of the plates for 3 days under 5% $CO_2$ at 37° C., a second layer of agar containing neutral red is added. Plaques are counted after incubation of the plates for another 12 to 24 h, and the specific infectivity is calculated as the number of PFU per microgram of RNA.

Growth curves. Subconfluent BHK-21 and C6/36 cells in 12-well plates are inoculated with WNV at an MOI of 5 or 0.05 in triplicate wells. Virus stocks are diluted in BA-1 (M199-H (Gibco-BRL), 0.05 M Tris, pH 7.6, 1% bovine serum albumin, 0.35 g of sodium bicarbonate/liter, 100 U of penicillin/ml, 100 µg of streptomycin/ml, and 1 µg of amphotericin B (Fungizone)/ml). Attachment is allowed for 1 h under 5% $CO_2$ at 37° C. or under 5% $CO_2$ at 28° C. for the BHK-21 and C6/36 cells, respectively. The inocula are then removed, the monolayers are washed three times with BA-1, and 2 ml of medium is added to each well. The plates are incubated for up to 6 days under 5% $CO_2$ at 37° C. or under 5% $CO_2$ at 28° C. for the BHK-21 and C6/36 respectively. The medium is sampled at 1, 7.5, 16, 24, 32, 40, 48 and 72 h for BHK-21 and C6/36 cells, as well as at 96 and 124 h for C6/36 cells. The 10-µl samples are stored at −80° C. prior to titration as previously described (Reisen, et al., supra). Cells are observed daily for CPE.

Virulence in mice. Mice are housed in an environmentally controlled room under biosafety level 3 conditions and are given food and water ad libitum. Female outbred CD-1 mice (Charles River Laboratories, Wilmington, Mass.) are obtained at 5 weeks of age and acclimatized for 1 week. All mice are 6 weeks of age at the start of the experiment. Eight mice per group are inoculated with diluent alone or with $10^2$ PFU of virus subcutaneously (s.c.) in the left rear footpad. Diluent is PBS (endotoxin-free) supplemented with 1% FBS. Mice are evaluated clinically and weighed daily for 2 weeks, then monitored daily and weighed thrice weekly for 2 more weeks. Observed clinical signs include ruffled fur, paresis, hindleg paralysis, and tremors. Morbidity is defined as exhibition of greater than 10% weight loss or clinical signs for 2 or more days. Mice are euthanized if they become moribund. Exposure to virus is confirmed in all surviving mice by a positive antibody titer to WNV by enzyme-linked immunosorbent assay on day 28 postinoculation.

REFERENCES

1. A. Wasley, M. J. Alter, Semin. Liver Dis. 20, 1 (2000).
2. Reed, et al., in Hepatitis C Virus, Reesink, Ed. (Karger, Basel, 1998), vol. 1, chap. 1, p. 55-84.
3. V. Lohmann, et al., Science 285, 110 (1999).
4. K. V. Konan et al., J. Virol. 77, 7843 (2003).
5. S. T. Shi, K. J. Lee, H. Aizaki, S. B. Hwang, M. M. Lai, J. Virol. 77, 4160 (2003).
6. N. El-Hage, G. Luo, J. Gen. Virol. 84, 2761 (2003).
7. J. L. Goldstein, M. S. Brown, Nature 343, 425 (1990).
8. F. L. Zhang, P. J. Casey, Annu. Rev. Biochem. 65, 241 (1996).
9. R. W. Mahley, T. P. Bersot, in Goodman and Gilman's The Pharmacological Basis of Therapeutics, J. G. Hardman, et al., Eds. (McGraw-Hill Pub., New York, 2001), pp. 971-1002.
10. K. H. Muntz, P. C. Sternweis, A. G. Gilman, S. M. Mumby, Mol. Biol. Cell 3, 49 (1992).
11. M. Ikeda, M. Yi, K. Li, S. M. Lemon, J. Virol. 76, 2997 (2002).
12. E. Foy et al., Science 300, 1145 (2003).
14. J. Ye, C. Wang, M. S. Brown, J. L. Goldstein, M. Gale, Jr., unpublished observations.
15. K. K. Chan, A. M. Oza, L. L. Siu, Clin. Cancer Res. 9, 10 (2003).
16. V. Lohmann, et al. J. Virol. 77, 3007 (2003).
17. M. S. Brown, J. L. Goldstein, J. Lipid Res. 21, 505 (1980).
18. L. Ellgaard, A. Helenius, Nat. Rev. Mol. Cell Biol. 4, 181 (2003).
19. E. C. Lerner, Y. Qian, A. D. Hamilton, S. M. Sebti, J. Biol. Chem. 270, 26770 (1995).
20. D. Wang, X. Yu, P. Brecher, J. Biol. Chem. 273, 33027 (1998).
21. G. L. James, M. S. Brown, M. H. Cobb, J. L. Goldstein, J. Biol. Chem. 269, 27705 (1994).
22. B. B. Bordier et al., J. Virol. 76, 10465 (2002).
23. A. I. Su et al., Proc. Natl. Acad. Sci. U.S.A 99, 15669 (2002).
24. M. S. Brown, J. L. Goldstein, Cell 89, 331 (1997).
25. N. Enomoto et al., N. Engl. J. Med. 334, 77 (1996).
26. J. G. McHutchison, K. Patel, Hepatology 36, S245 (2002).
27. X. Forns, J. Bukh, Clin. Liver Dis. 3, 693 (1999).
28. P. Farci et al., Proc. Natl. Acad. Sci. U.S.A. 99, 3081 (2002).
29. N. Enomoto et al., N. Engl. J. Med. 334, 77 (1996).
30. S.-L. Tan, A. Pause, Y. Shi, N. Sonenberg, Nature Reviews Drug Discovery 1, 1 (2002).
31. A. Staal et al., J. Bone Min. Res. 18, 88 (2003).

The foregoing examples are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for reducing permissiveness of human cells to replication of a human pathogenic Flaviviridae virus predetermined (I) to lack any C-terminal CXXX box; (ii) to lack prenylated viral protein, and (iii) to be replication-dependent on host protein prenylation, the method comprising steps:
   (a) contacting human cells subject to infection by the virus with an effective amount of a selective inhibitor of a prenylation enzyme of the cells, wherein the enzyme is selected from the group consisting of an HMG CoA reductase and a prenyltransferase; and
   (b) confirming a resultant reduction in permissiveness of the cells to replication of the virus.

2. The method of claim 1, wherein the enzyme is HMG CoA reductase.

3. The method of claim 1, wherein the enzyme is HMG CoA reductase and the inhibitor is selected from the group consisting of: atorvastatin (Lipitor), pravastatin (Pravachol), lovastatin (Mevacor), simvastatin (Zocor), fluvastatin (Lescol) and rosuvastatin calcium (Crestor).

4. The method of claim 1, wherein the enzyme is geranylgeranyl transferase I (GGTase I).

5. The method of claim 1, wherein the enzyme is geranylgeranyl transferase I (GGTase I), and the inhibitor is selected from the group consisting of: GGTI-286, GGTI-298, Massadine, and a Candida albicans GGTase I inhibitor.

6. The method of claim 1, wherein the virus is a hepatitis C virus (HCV).

7. The method of claim 2, wherein the virus is a hepatitis C virus (HCV).

8. The method of claim 3, wherein the virus is a hepatitis C virus (HCV).

9. The method of claim 4, wherein the virus is a hepatitis C virus (HCV).

10. The method of claim 5, wherein the virus is a hepatitis C virus (HCV).

11. The method of claim 1, wherein the virus is a West Nile virus (WNV).

12. The method of claim 2, wherein the virus is a West Nile virus (WNV).

13. The method of claim 3, wherein the virus is a West Nile virus (WNV).

14. The method of claim 4, wherein the virus is a West Nile virus (WNV).

15. The method of claim 5, wherein the virus is a West Nile virus (WNV).

* * * * *